Figure 1:
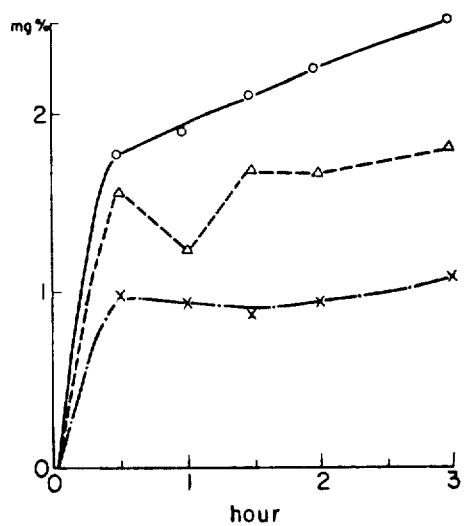

United States Patent [19]
Hori et al.

[11] 4,036,747
[45] July 19, 1977

[54] ADSORBENT FOR RECYCLING ARTIFICIAL KIDNEY

[75] Inventors: Masatake Hori; Shintaro Kikuchi, both of Hyogo, Japan

[73] Assignee: Takeda Chemical Industries, Ltd., Osaka, Japan

[21] Appl. No.: 589,835

[22] Filed: June 24, 1975

Related U.S. Application Data

[63] Continuation of Ser. No. 446,105, Feb. 26, 1974, abandoned.

[30] Foreign Application Priority Data

Feb. 27, 1973 Japan .................................. 48-23508

[51] Int. Cl.$^2$ ........................................... B01D 13/00
[52] U.S. Cl. .............................. 210/22 A; 210/321 B
[58] Field of Search ............... 210/40, 321 B; 282/317

[56] References Cited

U.S. PATENT DOCUMENTS

| 2,055,685 | 9/1936 | Flett ................................. 210/40 X |
| 2,062,075 | 11/1936 | Wallerstein ....................... 210/40 X |
| 3,183,194 | 5/1965 | Kuwata et al. ....................... 252/317 |
| 3,703,959 | 11/1972 | Raymond ..................... 210/321 B X |

*Primary Examiner*—Frank A. Spear, Jr.
*Attorney, Agent, or Firm*—Wenderoth, Lind & Ponack

[57] ABSTRACT

Removal of uremic wastes, such as creatinine, uric acid, phosphates, etc., from the artificial kidney dialyzate is satisfactorily conducted by employing an adsorbent comprising activated carbon and gel-type alumina.

1 Claim, 3 Drawing Figures

ADSORBENT FOR RECYCLING ARTIFICIAL KIDNEY

This application is a continuation of application Ser. No. 446,105, filed February 26, 1974 (now abandoned).

This invention relates to an absorbent for use in an artificial kidney of the recycle type and to a method of removing uremic wastes including creatinine, uric acid, phosphates, etc., from dialyzed fluid in an artificial kidney of the recycle type.

The adsorbents employable for this type of use are required to be capable of adsorbing all the principal uremic wasts. Among said uremic wastes are creatinine, uric acid, methylguanidien, phenols, phosphates and so-called middle molecules, the respective molecular weights of which are presumed to range from about 500 to about 2,000.

Although, as the adsorbent for this purpose, use has been made of activated carbon, most of the inorganic ions are only sparingly adsorbed on activated carbon. Of these inorganic ions, phosphate, in particular, is said to interfere with the metabolism of calcium when it occurs in excess in the body fluid, causing diseases of bones, hypertrophy of the parathyroid and other disorders especially to people of relatively young age.

Though it has been proposed to use an adsorbent containing activated carbon and alumina manufactured by calcination of aluminum hydroxide, the adsorbent can hardly be accepted as very effective for removingg inorganic phosphates from the dialyzate and, therefore, it is far from being satisfactory for the practical use.

The present inventors have surprisingly discovered that an adsorbent comprising activated carbon and gel-type alumina, especially in a form of mixture, shows a very remarkable effect for removing from the dialyzed fluid organic uremic wastes as well as inorganic phosphates. The above discovery is based on the following discovery that gel-type alumina is employed in combination with activated carbon whereby phosphate, which is harmful, can be removed whilst the inherent adsorptive affinity of activated carbon for organic uremic wastes is not thereby impaired.

Thus the present invention relates to an adsorbent for use in an artificial kidney of the recycling type, which comprises activated carbon and gel-type alumina, and to a method of removing uremic wastes from the dialyzed fluid with the adsorbent to remove in an artificial kidney of the recycle type.

The activated carbon may be of various conventional types, but steam-activated carbon based on sawdust, coal, coconut shell, etc. are particularly effective. The activated carbon may be any of powdered, pelletized and crushed one, but crushed one is preferable, for it is essential to ensure sufficient rigidity, which is regarded as an important quality in preventing entry of fine dust and fragmentation during the use thereof, and also to provide a sufficiently large surface area for adsorption. Grain size of these carbons is preferably within the range of about 10 to 200 meshes (Japanese pharmaceutical grade, abbreviated as J.P.). As to adsorptive capacity, the carbon is preferably able to adsorb at least 85 percent of creatinine and of uric acid, when these substances are used as typical metabolic wastes in an assay, (The assay is conducted in a similar manner as described in Experiment.).

The alumina manufactured by calcination of aluminum hydroxide is not gel-type one. This kind of alumina is practically useless for removing inorganic matter including phosphates even if it is employed together with activated carbon.

The inventors of this invention conducted studies on the above aspect of the problem and found that gel-type alumina is very effective in the removal of inorganic matter including phosphates and also that it is completely free from the foregoing disadvantages.

Gel-type alumina employable in this invention can be prepared by neutralizing an aqueous solution of an aluminum salt (for example, aluminum sulfate, aluminum chloride or other mineral acid salt) by the addition of an alkali (for example, ammonia, calcium carbonate, etc.) whilst the salt formed and other solutes are removed by aqueous washing, to obtain an alumina sol, then maintaining said sol in a hydrophobic medium (for example, hydrocarbons, halogenated hydrocarbons, spindle oil, etc.) under heating (for example, 70° C to 100° C), thereby causing it to age into a gel and finally drying the same and in this connection, it should be understood that up to about 30 percent of silica may be added in the above process.

The method of the production of gel-type alumina are concretely exemplified By Journal of the Petroleum Society (Sekiyu Gakkai Shi 8, 604(1965)), U. S. Pat. Spec. Nos. 3,330,774 and 3,183,194. Alumina of this gel type is exemplified by NEOBEAD available from Mizusawa Kagaku Kogyo K. K. (Mizusawa Industrial Chemicals, Ltd., Japan).

In this invention, the finer the grains of gel-type alumina, the greater is the efficiency with which it adsorbs phosphates, but lest it should hinder the circulation of dialyzate, its grain size is preferably within the range of about 10 to 200 meshes (J.P.) and, for better results, about 16 to 100 meshes, just as in the case with the single use of the activated carbon. Since these grains are such that the internal phase of each grain is a gel-like bound structure, they have an extremely high rigidity as high as 80 to 120 kg./grain, so that the tendency of the grains to fragmentation during use is reduced to the minimum or, substantially speaking, these grains are not fragmented at all. Because each grain is gel-like and has an internal porosity of molecular dimensions, its adsorptive affinity for phosphate is by far greater than other commercial grades of alumina despite its size and rigidity.

The amounts of activated carbon and gel-type alumina to be used in artificial kidney depend upon the kind and seriousness of the diseases and the number of dialytic cycles. Generally speaking, however, the amounts are selected with reference to the amounts of creatinine (1 to 2g.), uric acid (0.5 to 1 g.) and phosphate (1 to 1.5 g. in terms of phosphor) daily excreted by man. However, since activated carbon can adsorb uremic wastes as methylguanidine, phenols, so-called middle molecules and the urotoxins whose structures remain yet to be elucidated, as well as creatinine and uric acid, it is desirable to employ 3 to 10 times the theoretically required amount of the activated carbon. The ratio of activated carbon to gel-type alumina which is to be used is generally in the rang of 10:1 to 10:10, more preferably 10:2 to 10:4 for each dialysis. The amount of activated carbon as such is in the range of 100 to 1,000 g., more preferably 200 to 500 g. and the amount of gel-type alumina is in the range of 100 to 1,000 g. more preferably, 200 to 500 g./treatment, respectively for each dialysis.

Adsorbent of the present invention is packed into the column or cartridge, through which the dialyzate is allowed to pass and uremic waste is removed by adsorption. However, it is possible to fill a couple of independent columns with activated carbon and gel-type alumina, respectively, and allow the dialyzate to flow down the columns in succession. In the latter case, the order of treatment may be optional, i.e. activated carbon first and gel-type alumina second or vice versa.

The equipment in which the adsorbents of this invention are to be employed may be of any optional type insofar as it has a device for recycling the dialyzate. A column or columns packed with these adsorbents is/are interposed at a suitable position in the circuitry so that the dialyzate containing toxic substances may flow through it/them and be thereby adsorbed. The dialyzer to be used in combination with this device may be any known equipment, for example any of the Kiil, Kolff, hollowfiber and other types.

For further explanation of the present invention the following Experiments and Example are given.

EXPERIMENT 1

Preparation of the Control Solution for the Experiment

An aqueous solution which contains the following components:

20.253 g/dl of NaCl
0.522 g/dl of KCl
0.643 g/dl of $CaCl_2.2H_2O$
0.534 g/dl of $MgCl_2.6H_2O$
15.718 g/dl of $CH_3COONa.3H_2O$ and
7.0 g/dl of glucose is further diluted with water to 35 times its volume.

In the thus diluted solution are dissolved 5 mg./dl of creatinine, 5 mg./dl of uric acid and 34.6 mg/dl of $Na_2HPO_4.12H_2O$. (3 mg/dl as phosphor)

PREPARATIONS OF EXPERIMENTAL MATERIALS (I)

I.-i. activated carbon (manufactured by Takeda Chemical Industries. Ltd., Japan; crushed carbon, 28 to 80 mesh (J.P.)) (0.5 g.)

I.-ii. non-gel type alumina (manufactured by REYNOLDS Metals, Co., U.S.A. (0.2 g.)

I.-iii. gel-type alumina (NEOBEAD-C containing 0 % of silica, manufactured by Mizusawa Industrial Chemicals, Ltd., Japan) (0.2 g.)

I.-IV. non-gel type alumina (same as above (ii)) (0.2 g.) and activated carbon (same as above (i) (0.5 g.)

I.-v. gel-type alumina (same as above (iii)) (0.2 g.) and activated carbon (same as above (i)) (0.5 g.).

Method of Experiment

To 30 ml. each of the solution of the Control Solution are added the respective materials derived above. The respective mixtures are shaken at 37° C. for 15 hours for allowing creatinine, uric acid and $Na_2HPO_4$ to be adsorbed on the respective materials as far as possible.

The non-adsorbed creatinine is measured by a similar manner as described in Henry R. J., Clinical Chemistry 12, 278-302(1966) (Colorimetry), and the non-adsorbed uric acid is measured by a similar manner as described in Wendell T. Caraway et al, Standard Methods of Clinical Chemistry 4, 239-247(1963) (Colorimetry), and the remaining phosphate (as converted to phosphor) is measured by a similar manner discribed in Fiske C. H. and Subbarow Y., Journal of Biological Chemistry 66, 375-400(1925).

EXPERIMENT 2

Preparation of the Control Solution for the Experiment

The same as that of Experiment 1.

Preparation of Experimental Materials (II) for adsorbent

II.-i. gel-type alumina (NEOBEAD-DL containing 10% by weight of silica, manufactured by Mizusawa Industrial Chemicals, Ltd., Japan) (0.2 g.) and activated carbon (same as (I)-(ii)) (0.5 g.)

II.-ii. gel-type alumina (NEOBEAD which contains 30% by weight of silica, manufactured by Mizusawa Industrial Chemicals, Ltd., Japan) (0.2 g.) and activated carbon (same as (I)-(i)) (0.5 g.)

Method of Experiment

The same as that of Experiment 1.

Results of Experiment 1 and 2 are shown in Table 1.

Table 1

| Adsorbent | Equilibrium adsorption (%) | | |
|---|---|---|---|
| | creatinine | uric acid | $Na_2HPO_4$ |
| I-(i) | 81.4 | 85.7 | 2.0 |
| I-(ii) | 3.1 | 4.2 | 28.7 |
| I-(iii) | 2.8 | 4.1 | 59.3 |
| I-(iv) | 81.5 | 84.2 | 37.2 |
| I-(v) | 82.8 | 86.3 | 61.9 |
| II-(i) | 82.4 | 86.8 | 67.0 |
| II-(ii) | 81.7 | 85.9 | 65.2 |

Frome the above Experiments, the adsorbability of the adsorbent comprising gel-type alumina and activated carbon is far more effective than those of the respective adsorbents of activated carbon, of gel type alumina, and of the combination of non-gel type of alumina and activated carbon.

Therefore, the adsorbent of the combination of gel-type alumina and activated carbon is very useful as an adsorbent for artificial kidney.

EXAMPLE 1

Three dogs (body weight: about 10 kg.) in which experimental uremia has been induced by ureteal ligation is treated by use of an artificial kidney of the recycle type and the changes in concentration of creatinine, uric acid and phosphates (as coverted to the concentration of phospher) are measured at timed intervals during the dialysis. The conditions of dialysis:

a. Dialyzing fluid: 7.51. L (AK-Solita (manufactured by Shimizu Seiyaku Kabushiki Kaisha, Japan), the same solution as the "aqueous solution of Experiment 1, preparation of the Control Solution", 1:35 dilution, 37° C)

b. Pressure of dialysis: −90 mmHg.

c. Circulation rate of dialyzate: 300–400 ml/min.

d. Adsorbents:

i. Only the activated carbon (150 g.)

ii. The activated carbon (manufactured by Takeda Chemical Industries, Ltd., Japan; powdered carbon, 28 to 80 mesh (J. P.) (150 g.) plus the gel-type alumina (NEOBEAD-DL containing 10% by weight of silica, manufactured by Mizusawa Industrial Chemicals, Ltd., Japan) (90 g.). The adsorbents are packed into a column, about 80 cm in diameter.

e. Equipment used: DIFAK prototype artificial kidney of recycle type (manufactured by Kabushiki Kaisha Musashi-Engineering, Japan)

f. Membrane: One commercial hollowfiber membrane (hollowfiber artificial kidney model-3, manufactured by Cordis Dow, Co., U.S.A.)

Figure 2:
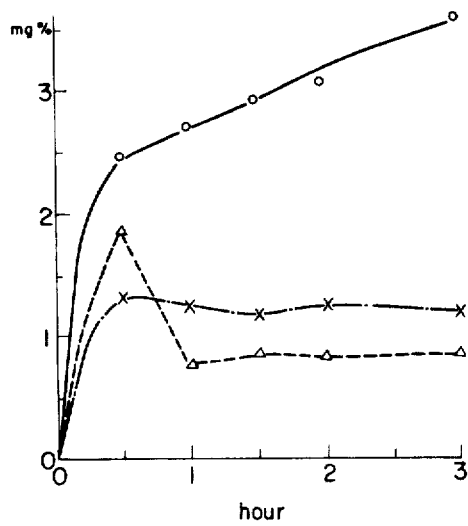
Figure 3:
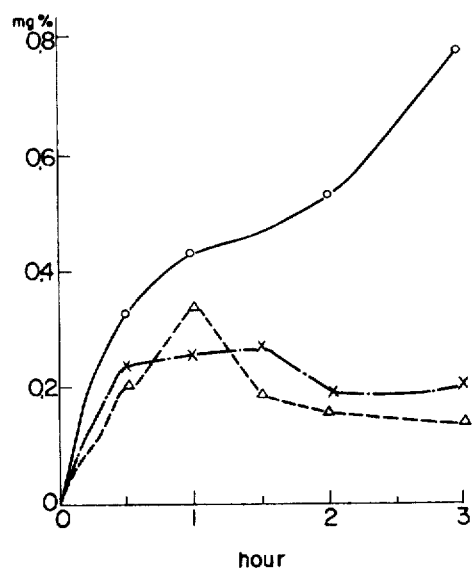

The results are shown in FIGS. 1, 2 and 3.

Measured by a similar manner to the above Experiment.

Concentrations of creatinine and uric acid in the dialyzate are drastically reduced in both the cases of using activated carbon alone and co- using of activated carbon and gel-type alumina, when compared with the results for the control, indicating the effectiveness of these adsorbents. As regards phosphate, even the use of activated carbon alone is conducive to slight reductions as compared with controls but the reductions attained by the combined use of activated carbon and gel-type alumina are more pronounced, clearly indicating the effectiveness of the adsorbents according to this invention.

In the attached FIGS., FIG. 1 shows an adsorbancy of phosphate (as converted to the concentration of phosphor) in the dialyzing fluid, FIG. 2 shows an adsorbancy of creatinine in the dialyzing fluid, and FIG. 3 shows an adsorbancy of uric acid in the dialyzing fluid.

In the attached FIGS., the meaning of the symbol —Δ—, —x— and —o— are as follows:

—Δ—: Adsorbent comprises activated carbon only.

—x—: Adsorbent comprises a mixture of activated carbon and gel-type alumina.

—o—: Control

The meaning of "mg %" is "mg. in 100 ml. of the solution."

What we claim is:

1. In a method for removing uremic wastes from dialyzed fluid in an artificial kidney of the recycle type which comprises treating artificial kidney dialyzate with an adsorbent, the improvement according to which the adsorbent consists essentially of activated carbon and gel-type alumina, the ratio of activated carbon to gel-type alumina being 10:1 to 10:10 by weight, the gel-type alumina employed being that produced by the process which comprises neutralizing an aqueous solution of an aluminum salt by the addition of an alkali, removing the salt formed and other solutes by aqueous washing to obtain an alumina sol, maintaining said sol in a hydrophobic medium under heating to thereby cause it to age into a gel and drying the said gel, the gel-type alumina containing silica in an amount of from 0 to 30% by weight.

* * * * *